(12) United States Patent
Sternby et al.

(10) Patent No.: US 9,067,027 B2
(45) Date of Patent: *Jun. 30, 2015

(54) FLOW REVERSING DEVICE AND FLUID TREATMENT APPARATUS

(71) Applicant: GAMBRO LUNDIA AB, Lund (SE)

(72) Inventors: Jan Peter Sternby, Lund (SE); Eddie Nilsson, Hoor (SE); Lennart Jönsson, Bjarred (SE)

(73) Assignee: Gambro Lundia AB, Lund (SE)

( * ) Notice: Subject to any disclaimer, the term of this patent is extended or adjusted under 35 U.S.C. 154(b) by 33 days.

This patent is subject to a terminal disclaimer.

(21) Appl. No.: 14/064,776

(22) Filed: Oct. 28, 2013

(65) Prior Publication Data

US 2014/0048161 A1    Feb. 20, 2014

Related U.S. Application Data

(63) Continuation of application No. 12/665,453, filed as application No. PCT/IB2007/001754 on Jun. 27, 2007, now Pat. No. 8,568,346.

(51) Int. Cl.
*A61M 37/00* (2006.01)
*A61M 1/36* (2006.01)
*A61M 39/22* (2006.01)

(52) U.S. Cl.
CPC ........ *A61M 1/3663* (2013.01); *Y10T 137/86839* (2015.04); *A61M 1/3653* (2013.01); *A61M 1/367* (2013.01); *A61M 39/223* (2013.01); *A61M 1/3656* (2014.02)

(58) Field of Classification Search
CPC ............ A61M 1/3653; A61M 1/3656; A61M 1/3663; A61M 1/367; A61M 39/233

USPC ............... 604/4.01, 5.01, 5.04, 6.1, 9, 93.01, 604/96.01, 500, 507; 422/44; 210/228, 298, 210/304, 149.8; 137/597, 625.43–625.48
See application file for complete search history.

(56) References Cited

U.S. PATENT DOCUMENTS

| | | | |
|---|---|---|---|
| 3,905,275 | A | 9/1975 | Saida et al. |
| 5,549,582 | A | 8/1996 | Larsson et al. |
| 5,605,630 | A | 2/1997 | Shibata |
| 5,819,775 | A | 10/1998 | Holloway |
| 5,894,011 | A | 4/1999 | Prosl et al. |
| 5,931,163 | A | 8/1999 | Stegmann et al. |
| 6,177,049 | B1 | 1/2001 | Schnell et al. |

(Continued)

FOREIGN PATENT DOCUMENTS

| EP | 1 017 443 A1 | 7/2000 |
|---|---|---|
| EP | 1 090 655 A1 | 4/2001 |

(Continued)

OTHER PUBLICATIONS

MERCADAL Lucile el al., "Determination of access blood flow from ionic dialysance: Theory and validation", Kidney International, vol. 56, 1999, pp. 1580-1565.

*Primary Examiner* — Philip R Wiest
(74) *Attorney, Agent, or Firm* — K&L Gates LLP

(57) ABSTRACT

The invention relates to a multi-ports extracorporeal medical device (1) having a selector body (19) which can be linearly displaced within the housing (16) in order to create different flow paths and connection among the ports. The device can for instance be used for reversing the flow in an extracorporeal blood circuit.

10 Claims, 10 Drawing Sheets

(56) References Cited

U.S. PATENT DOCUMENTS

| | | |
|---|---|---|
| 6,189,388 B1 | 2/2001 | Cole et al. |
| 6,269,839 B1 | 8/2001 | Wickham et al. |
| 6,308,737 B1 * | 10/2001 | Krivitski .................. 137/597 |
| 6,319,465 B1 | 11/2001 | Schnell et al. |
| 6,565,525 B1 | 5/2003 | Burbank et al. |
| 6,695,807 B2 | 2/2004 | Bell et al. |
| 6,793,194 B1 | 9/2004 | Grinberg |
| 6,830,073 B2 | 12/2004 | Lee |
| 7,121,291 B2 | 10/2006 | Sueda |
| 8,568,346 B2 * | 10/2013 | Sternby et al. ............ 604/4.01 |
| 2005/0124943 A1 | 6/2005 | Yang |
| 2005/0131335 A1 | 6/2005 | Drott et al. |
| 2006/0079827 A1 | 4/2006 | Jensen et al. |
| 2006/0161094 A1 | 7/2006 | Utterberg et al. |

FOREIGN PATENT DOCUMENTS

| | | |
|---|---|---|
| FR | 2 289 451 A1 | 2/2007 |
| GB | 1 212 408 A | 11/1970 |
| WO | 95/00194 A1 | 1/1995 |
| WO | 98/51368 A1 | 11/1998 |
| WO | 03/029706 A1 | 4/2003 |

* cited by examiner

FLOW REVERSING DEVICE AND FLUID TREATMENT APPARATUS

FIELD OF THE INVENTION

The invention relates flow reversing device and fluid treatment apparatus adopting said flow reversing device.

BACKGROUND OF THE INVENTION

In many applications fluid flowing in a conduit may need to be treated by a treatment unit outside the conduit and then returned to the same. In such cases part or all the fluid is withdrawn from the conduit in correspondence of an upstream portion of the conduit, treated by the treatment unit and then returned to the conduit in a downstream portion of the same conduit. In certain cases it may be needed to withdraw the fluid from the downstream portion and return it to the upstream portion of the conduit. In these cases where the flow withdrawal and flow return areas may need to be switched, it can be convenient to adopt flow reversing systems which allow an easy commutation between the two configurations.

Referring by way of non limiting example to extracorporeal blood treatments, it is known removing blood from a patient by means of an arterial set, passing of the blood to a blood processing device such as a dialyzer, and returning of the blood to the patient again through a venous blood set. The venous and arterial lines create the communication of blood between a vascular access on the patient and the blood processing device. In order to monitor the patient access site it can be convenient to switch the arterial and venous lines between a first configuration, where blood is withdrawn from an upstream portion of the vascular access and returned to a downstream portion of the same, and a second configuration, where blood is withdrawn from a downstream portion of the vascular access and returned to an upstream portion of the same.

Also in this case it is useful adopting flow reversal devices which allow easy commutation between the two mentioned configurations without need of connecting and disconnecting the lines from the patient.

Devices capable of enabling flow inversion at the patient-side suction and delivery branches, while keeping the circulation flow within the filtering unit unchanged have been also developed.

A first known device is disclosed in the publication Kidney International Vol. 56, 1999, page 1564, FIG. 6 and in U.S. Pat. No. 6,189,388, again in FIG. 6, as well as in the French publication FR2889451 and consists in a set of four tube portions where 2 parallel tube portions are connected via two transversal tube portions. Clips are provided on each tube portion.

U.S. Pat. No. 6,695,807 and US2006161094 show flow reversal systems including arterial and venous lines+2 transverse tubes to form a square-shaped ring. A switching device can act on the square shaped ring to open and close selectively the four tube portions forming the ring.

U.S. Pat. No. 6,308,737 discloses an inverter device interposed between the vascular access to the patient and the blood pump, and the dialyser capable of enabling a flow inversion in the blood circuit portion directly in communication with the patient's vascular system while keeping the extracorporeal blood flow within the dialyser unchanged.

The inverter in particular comprises a deformable chamber provided with a plurality of ports. By deforming the chamber along a predetermined direction, a fluid communication between the pre-established ports is created while a fluid communication between other ports is prevented.

In particular, by suitably studying the connections of the extracorporeal blood circuit with the chamber doors and the deformations to be imposed to the chamber itself a flow inversion as above stated is obtained.

U.S. Pat. No. 5,894,011 discloses a device for flow inversion in haemodialysis apparatus. This device comprises two discs such interconnected that they can rotate relative to each other without separating. The two discs have appropriate fluid accesses, those of one disc being susceptible of connection with the blood lines directly associated with the patient and those of the other disc being susceptible of direct connection with the blood lines in fluid communication with the filtering unit. The two discs can take at least two relative angular positions; in a first position they enable passage of the blood flow in a first direction of direct circulation, in the other position (in which they are rotated relative to each other) they allow an inverted circulation flow in the circuit. In particular in the second inverted configuration the blood suction line from the patient in the first position becomes the delivery line of same and correspondingly, the delivery line of the first position becomes the suction line in the second position.

U.S. Pat. Nos. 6,177,049 and 6,319,465 disclose two further typologies of flow inverting valves both to be positioned between the vascular accesses to the patient and the blood pump and filtering unit. The first patent teaches use of a fixed external valve body to the inside of which an appropriate insert is connected which is capable of being moved between a first direct-circulation configuration and a second reverse circulation configuration. In particular, in the second reverse-circulation condition the suction line and delivery line at the vascular access to the patient are inverted with each other with respect to the first direct-flow condition. The second patent too shows a valve capable of exactly performing the same functions as the first patent, this valve being however made up of two halves coupled with each other so that they have a degree of freedom in rotation and, through mutual rotation of the two halves, a first direct-flow condition and a second reverse-flow condition are obtained at the vascular access to the patient.

US20060079827 shows a flow reversal valve having valve portions rotatably secured to one another, and detent features enabling audible or tactile feedback to a clinician or alignment features, such as visible indicators, on either side of the valve to confirm normal or reverse flow.

A further device for flow inversion in accordance with the U.S. Pat. No. 5,605,630 is also known. However this device is not used to invert the circulation flow at the vascular accesses to the patient, but to enable flow inversion within the filtering unit. In other words, the blood flow is inverted within the filtering unit intermittently and simultaneously the flow of the dialysis liquid is inverted within the same in such a manner that counter-current conditions are maintained therein. The above is carried out for quite different purposes from those of the present invention, i.e. to avoid blood clotting within the filter for dialysis.

SUMMARY OF THE INVENTION

All the devices briefly mentioned above however appeared to be susceptible of improvements under different points of view.

Accordingly, it is one object of the present invention to overcome some limits of the known art.

A further object of the invention is providing a flow reversing device which can be easily and quickly actuated.

Another object of the invention is providing a flow reversing device which can be operated without creating or at least significantly limiting problems of stagnation and clotting.

According to one embodiment of the invention, the device may be actuated very simply with only one hand (if manual actuation is used) or with a very simple actuator (if automated actuation is required).

A further aim of the invention is to provide a fluid treatment apparatus adopting the new flow reversing device of the invention.

When the invention is used with extracorporeal blood treatment apparatus, is a further aim of the invention to provide a circuit and a device for flow inversion capable of maintaining the blood flow within the filtering unit even following inversion of the flow at the vascular accesses to the patient.

It is then an auxiliary aim of the invention to provide a device for flow inversion of different structure and conception as compared with the devices hitherto on the market, which is cheap and reliable.

One or more of the foregoing aims are substantially achieved by a flow reversing device and by a blood treatment apparatus according to one or more of the appended claims.

Some aspects of the invention are below summarized.

An extracorporeal medical device for reversing flow according to the invention comprises:
a housing (16) presenting at least four ports (12,13,14 and 15) and a lateral wall (21) having an inner surface (22) radially delimiting an internal chamber (17),
a selector body (19) having at least an active portion (20) movable relative to the housing inside the internal chamber, between at least a first position and at least a second position, in said first position the active portion being positioned relative to the housing so that the first port (12) is in fluid communication with the second port (13) through said internal chamber (17) while the third port (14) is in fluid communication with the fourth port (15) through said internal chamber (17), and in said second position the active portion being positioned relative to the housing so that the first port (12) is in fluid communication with the fourth port (15) through said internal chamber (17) while the second port (13) is in fluid communication with the third port (14) through said chamber, characterized in that, as a consequence of the displacement of the selector body between the first and second position, the active portion of the selector body displaces at least axially along said inner surface of the lateral wall.

The device may include means (23) for linearly displacing the selector body between said first position and said second position, parallel to a longitudinal axis (18) of the internal chamber (17). The means for linearly displacing the selector body can be one or more, manually actionable, pushers (24) connected to the selector body or one or more actuators active on said selector body. Any suitable actuator acting directly or indirectly on the selector body can be adopted: for instance an hydraulic actuator, a pneumatic actuator, an electric actuator, an electromagnetic actuator cooperating with a magnetic or magnetizable portion of the selector body. A control unit may be connected to the actuator and control the actuator to move the selector body between said first and second positions.

The lateral wall inner surface (22) may have the shape of a generalized cylinder extending parallel to a longitudinal axis (18) of the internal chamber (17), the active portion of the selector body displacing axially, parallel to the inner surface of the lateral wall. For instance, the cross section of the inner surface (22) can be constant at least for a longitudinal portion of the internal chamber (17) equal or grater than an axial stroke of the selector body in the chamber between the first and second position. The cross section of the inner surface (22) may be shaped as a polygon, a circle, or an ellipse.

The ports (12,13,14,15) may be arranged on the lateral wall (21) and may present respective axis oriented transversally to the longitudinal axis of the internal chamber, for instance the ports axis may be perpendicular to the longitudinal axis of the internal chamber and lying on a common plane. The ports (12,13,14,15) can be symmetrically arranged on the lateral wall with respect to said longitudinal axis.

The housing can be in the shape of a tubular body presenting axially opposite open ends (50, 51).

The selector can include first and second terminals (52, 53) tightly coupled in a sliding manner to the lateral wall inner surface, said active portion extending between the first and second terminals. The first and second terminals (52, 53) present respective inner surfaces (57, 58), facing one another and cooperating with the active portion (20) of the selector and with a portion of the inner surface (21) of the housing to define at least two tightly separated fluid chambers (59, 60).

The selector active portion may comprise at least a first surface (54), facing the second port, a second surface (55), opposite the first surface and facing the fourth port, and a peripheral edge (56) tightly coupled in a sliding manner to internal wall. The first and second surfaces (54, 55) are continuous surfaces axially extending along and bending about the longitudinal axis (18). The peripheral edge (56) comprises two radially opposing edges (56a, 56b) extends axially, along the inner surface, in a non straight manner to define, in each of said first and second positions of the active portion, a non rectilinear seal line along said inner surface. Said first and second surfaces (54, 55) can be substantially in the shape of helicoids and each of the opposing edges (56a 56b) have substantially the shape of a cylindrical helix extending around the longitudinal axis (18). Alternatively, each of said first and second surface (54, 55) may present a first flat part, a second flat part (57,58) rotated (for instance perpendicular) with respect to the first flat part around said longitudinal axis, and a transition part joining the two flat parts; in this case the opposing edges (56a, 56b) comprises at least two parallel and transversally spaced portions (57a, 58a), which are interacting with the inner surface of the lateral wall in correspondence of circumferentially and axially spaced positions. In one solution (FIGS. 11-17) the portion may include two axially consecutive flat bodies (20a, 20b) axially guided inside the internal chamber and kept in angularly spaced positions by first and second guides (61, 62) slidingly receiving a respective of said flat bodies. The guides (61, 62) can be formed by through passages in the housing end walls, realizing a fluid tight coupling with the flat bodies and defining for each respective of said flat bodies a corresponding sliding plane, which is at an angle to the sliding plane of the other flat body. The end walls (63, 64) present respective inner surfaces, facing one another and cooperating, in each of said first and second positions, with the active portion of a corresponding one flat body of the selector and with a portion of the inner surface of the housing to define at least two tightly separated fluid chambers. The flat bodies comprise axially opposing edges (56a, 56b) presenting at least two parallel, and transversally spaced portions (57a, 58a), which are interacting with the inner surface of the lateral wall in correspondence of circumferentially and axially spaced positions.

The device may comprise (see embodiment of FIGS. 1a, 1b) a first deflector (71) housed in the internal chamber and facing the second port, the first deflector having at least a portion transversally oriented (e.g. parallel) with respect to an axis of said second port. The axially opposed ends of the first deflector can define stopcocks for the selector body. A second deflector (72) may also be housed in the internal chamber facing the fourth port, the second deflector having at least a portion transversally oriented (e.g. parallel) with respect to an axis of said first port. The axially opposed ends of the second deflector (72) can define stopcocks for the selector body.

The device may also be provided with a first tubing line (4a) having one end coupled to the first port and a second end provided with a connector, a second tubing line (4b) having one end coupled to the second port and a second end provided with a connector, a third tubing line (5a) having one end coupled to the third port and a second end provided with a connector, a fourth tubing line (5b) having one end coupled to the fourth port and a second end provided with a connector. The connectors on the first tubing line (4a) and on the third tubing line (5a) can be coupled with corresponding counter-connectors of access devices designed to be connected with a cardiovascular system of a living body. The connectors on the second tubing line (4b) and on the fourth tubing line (5b) can be coupled with corresponding counter-connectors of a treatment unit.

A blood processing apparatus according to the invention comprises the device having one or more of the features above summarized and at least one peristaltic pump (8) acting on a portion of at least one of said first, second, third and fourth tubing lines.

According to an independent aspect, a device for reversing flow according to the invention comprises:

a housing presenting at least three ports (12, 13, 14) and a lateral wall having an inner surface (22) radially delimiting an internal chamber (17), a selector body (19) having at least an active portion (20) movable relative to the housing inside the internal chamber, between at least a first position and at least a second position, in said first position the active portion being positioned relative to the housing so that the first port is in fluid communication with the second port through said internal chamber, and in said second position the active portion being positioned relative to the housing so that the first port is in fluid communication with the third port through said internal chamber, wherein said active portion comprises a first and a second opposed surfaces (54, 55) and a peripheral edge (56) radially and tightly coupled in a sliding manner to inner surface (22), said peripheral edge (56) comprising two radially opposing edges (56a, 56b), at least one of said radially opposing edges (56a, 56b) axially extending, along the inner surface, in a non straight manner.

The active portion may be axially movable between said first and second positions parallel to said lateral wall inner surface (22).

In one embodiment, the housing (16) presents at least four ports (12,13,14 and 15) the active portion in said first position is positioned relative to the housing so that the first port (12) is in fluid communication with the second port (13) through said internal chamber (17) while the third port (14) is in fluid communication with the fourth port (15) through said internal chamber (17), and in said second position the active portion is positioned relative to the housing so that the first port (12) is in fluid communication with the fourth port (15) through said internal chamber (17) while the second port (13) is in fluid communication with the third port (14) through said chamber.

The first and second surface (54, 55) can be continuous surfaces bending about the longitudinal axis (18) when axially moving along said the longitudinal axis. For example said first and second surfaces (54, 55) can be substantially in the shape of helicoids and the opposing edges (56a, 56b) have substantially the shape of a cylindrical helix axially extending around the longitudinal axis (18). Alternatively said first and second surface (54, 55) can present a first flat part and a second flat part (57, 58) joined by a transition part, the first flat part being transversal to the second flat part; each of the opposing edges (56a, 56b) comprises at least two parallel and transversally spaced portions (57a, 58a), which are interacting with the inner surface of the lateral wall in correspondence of circumferentially and axially spaced positions. According to a further alternative said active portion (20) may include two axially consecutive flat bodies (20a,20b) which are axially guided inside the internal chamber and kept in angularly spaced positions by first and a second guides (61, 62) obtained in the housing slidingly receiving a respective of said flat bodies. The housing may also present a first and a second end wall (63, 64) each extending on a respective side of the internal chamber transversally to the longitudinal axis, said guides being formed by through passages in said end walls realizing a fluid tight coupling with the flat bodies. The first and second end walls present respective inner surfaces, facing one another and cooperating with the active portion of the selector and with a portion of the inner surface of the housing to define at least two tightly separated fluid chambers; the flat bodies comprise the axially opposing edges (56a, 56b), each of the opposing edges presenting at least two parallel portions interacting with the inner surface of the lateral wall in correspondence of circumferentially and axially spaced positions.

SHORT DESCRIPTION OF THE DRAWINGS

Further features and advantages will be best understood from the detailed description of a preferred, but not exclusive embodiment of a flow reversing device and of a fluid treatment apparatus adopting said flow reversing device in accordance with the present invention. This description will be carried out hereinafter with reference to the accompanying drawings, given by way of non-limiting example, in which:

FIG. 1A an 1B are schematic longitudinal views of a first embodiment of a device for reversing flow in accordance with the invention, in a first and in a second operating condition;

DETAILED DESCRIPTION

Figure 9:
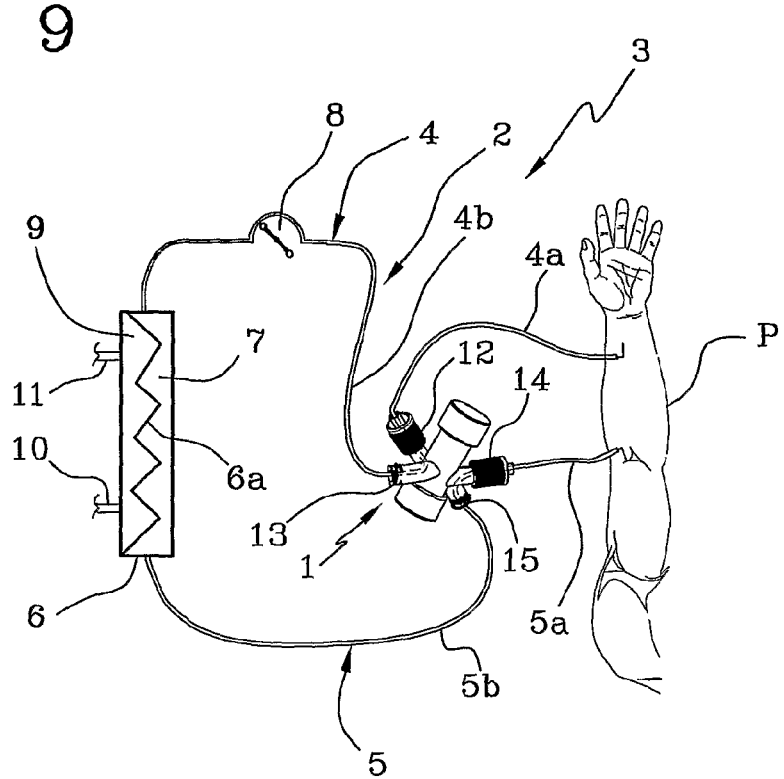
FIG. 9 is a schematic view of a blood processing apparatus connected to a patient and adopting a device according to the invention positioned in a first, or normal, position.
Figure 10:
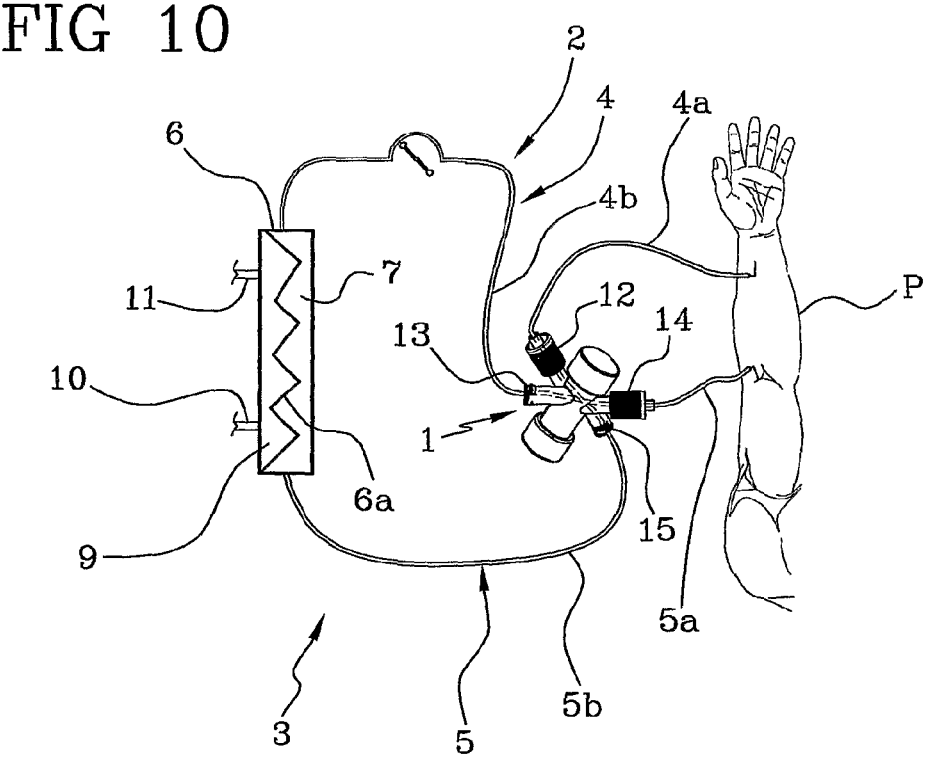
FIG. 10 is a schematic view of a blood processing apparatus connected to a patient and adopting a device according to the invention positioned in a second, or reverse, position.
Figure 11:
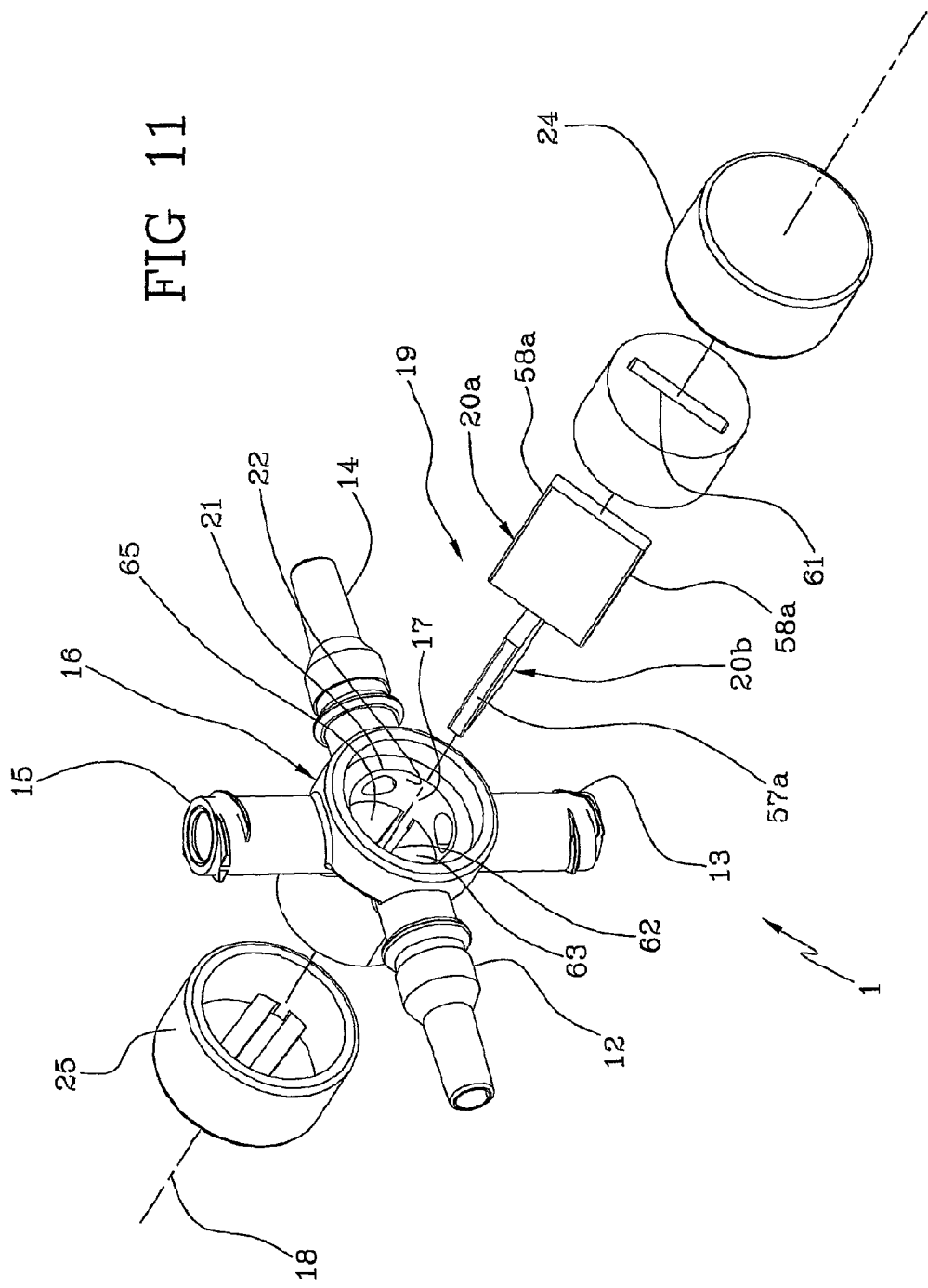
FIG. 11 is a perspective and exploded view of a third embodiment of a device of the invention.
Figure 12:
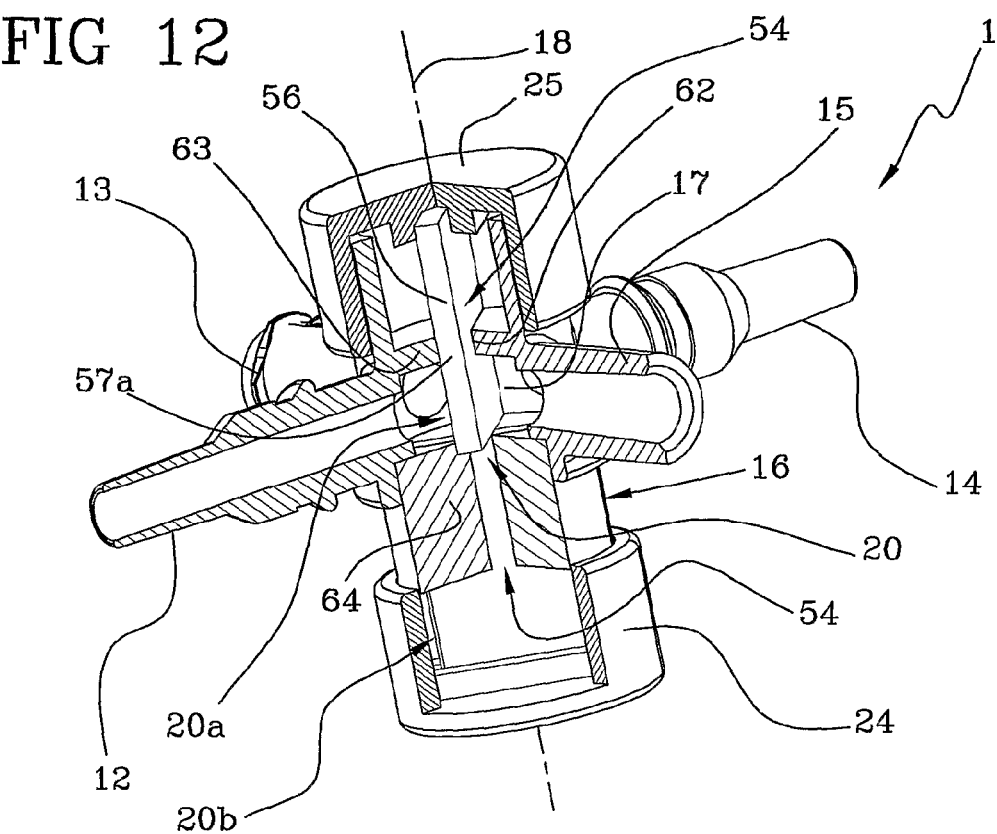
FIG. 12 is a partially sectioned perspective view of the third embodiment of a device for reversing flow in a first operating condition in accordance with the invention.
Figure 13:
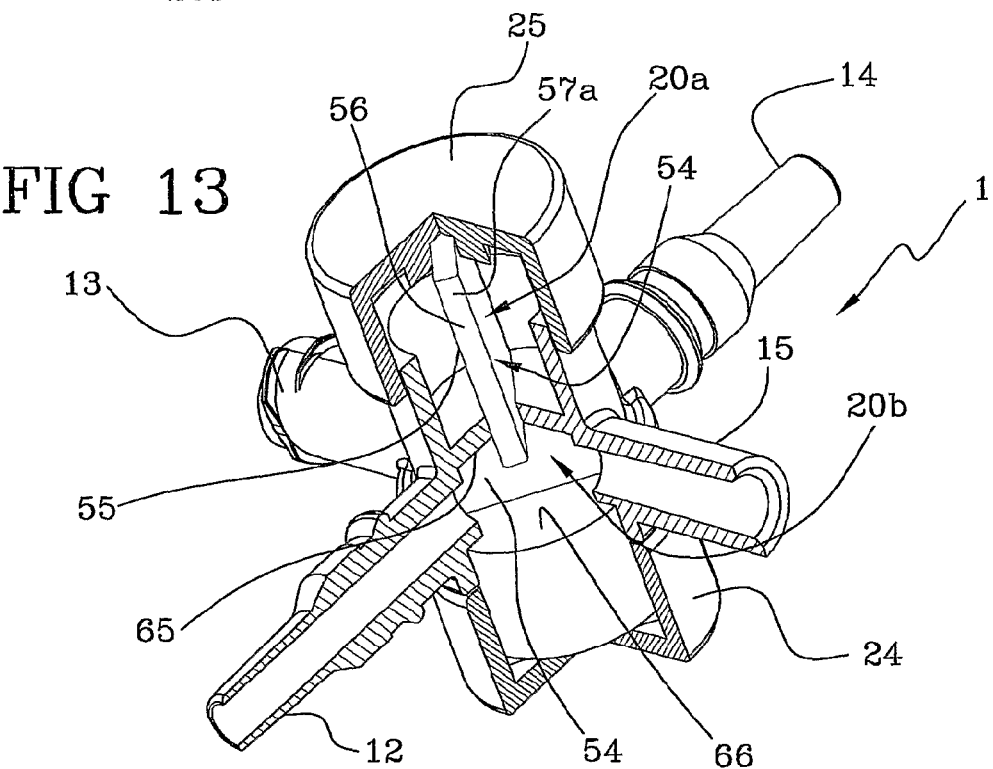
FIG. 13 is a partially sectioned perspective view of the third embodiment of a device for reversing flow in a second operating condition in accordance with the invention.
Figure 14:
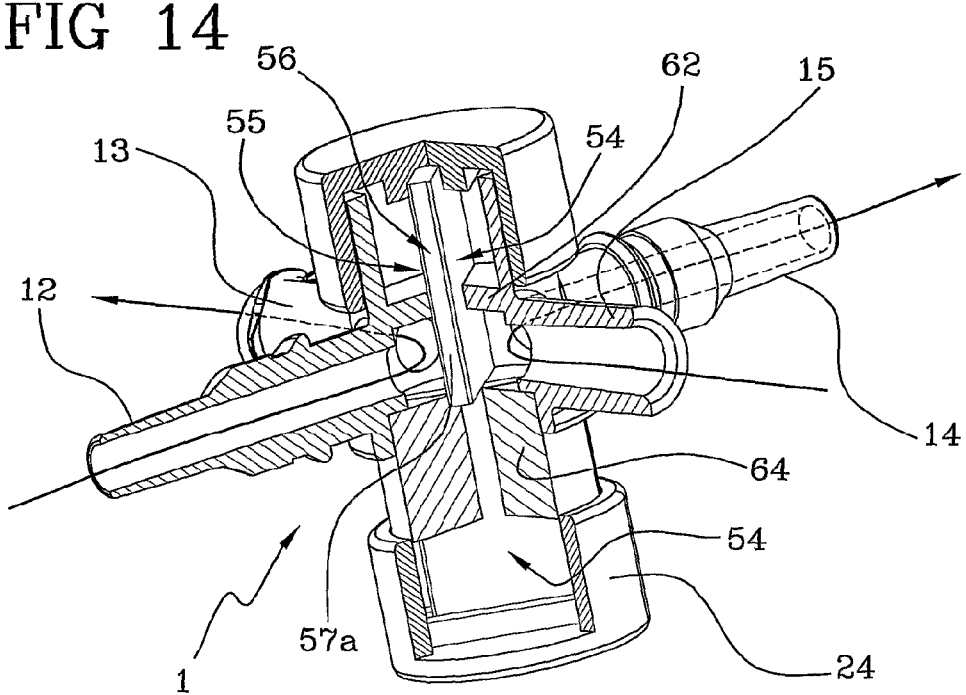
FIG. 14 shows the embodiment of FIG. 12 with arrows representing the circulation paths for the fluid.
Figure 15:
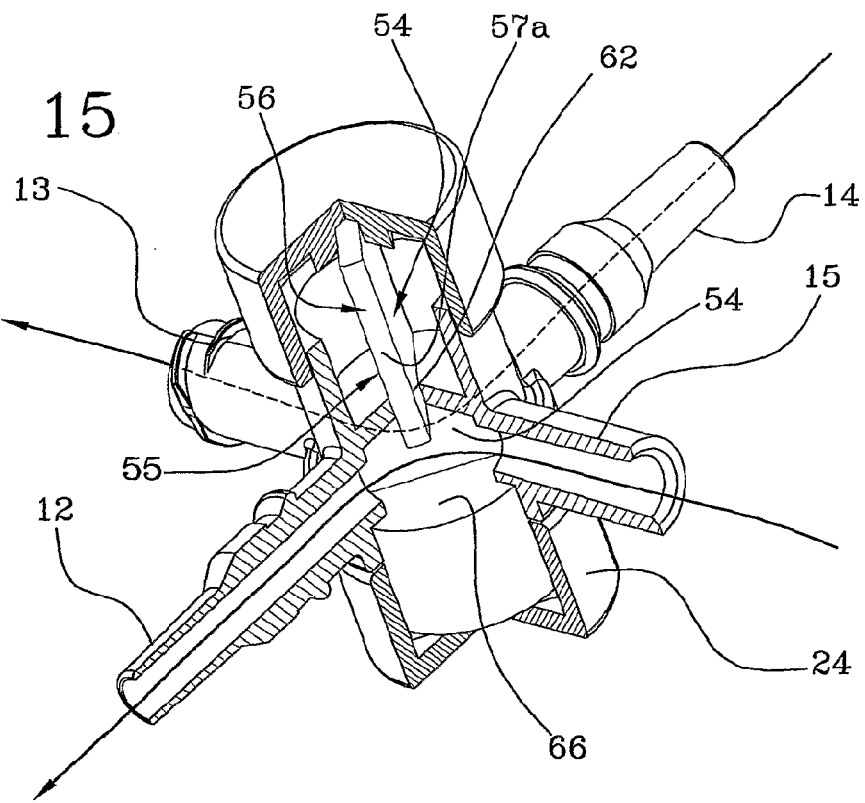
FIG. 15 shows the embodiment of FIG. 13 with arrows representing the circulation paths for the fluid.
Figure 16:
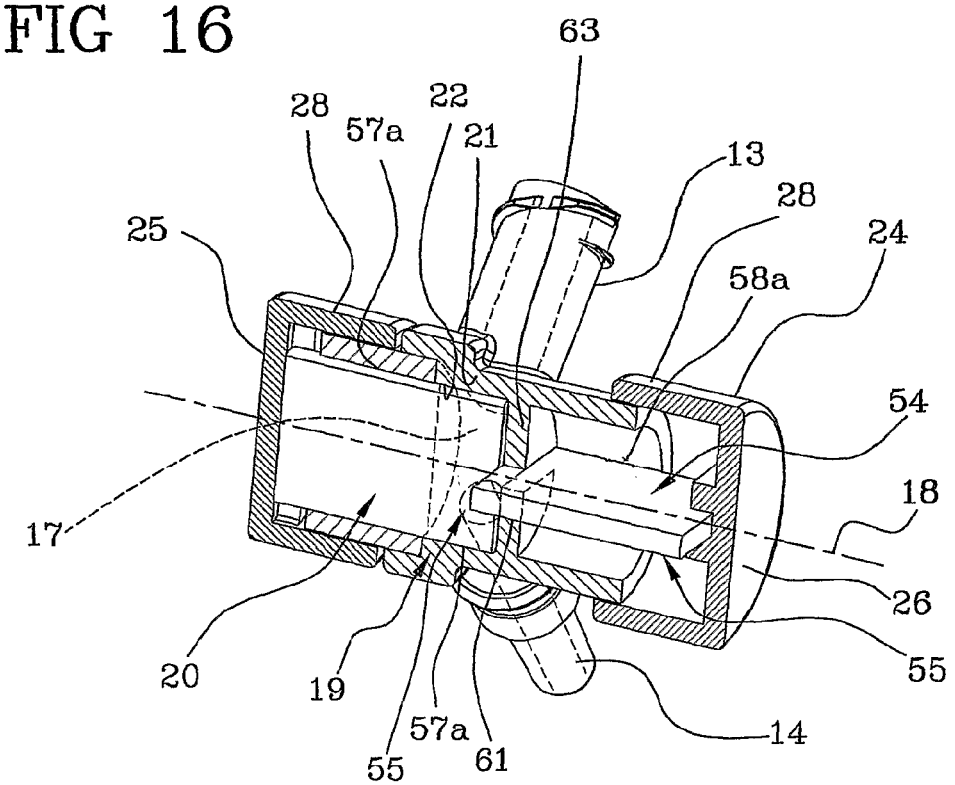
FIG. 16 is a longitudinally sectioned perspective view of the third embodiment shown in FIG. 13.
Figure 17:
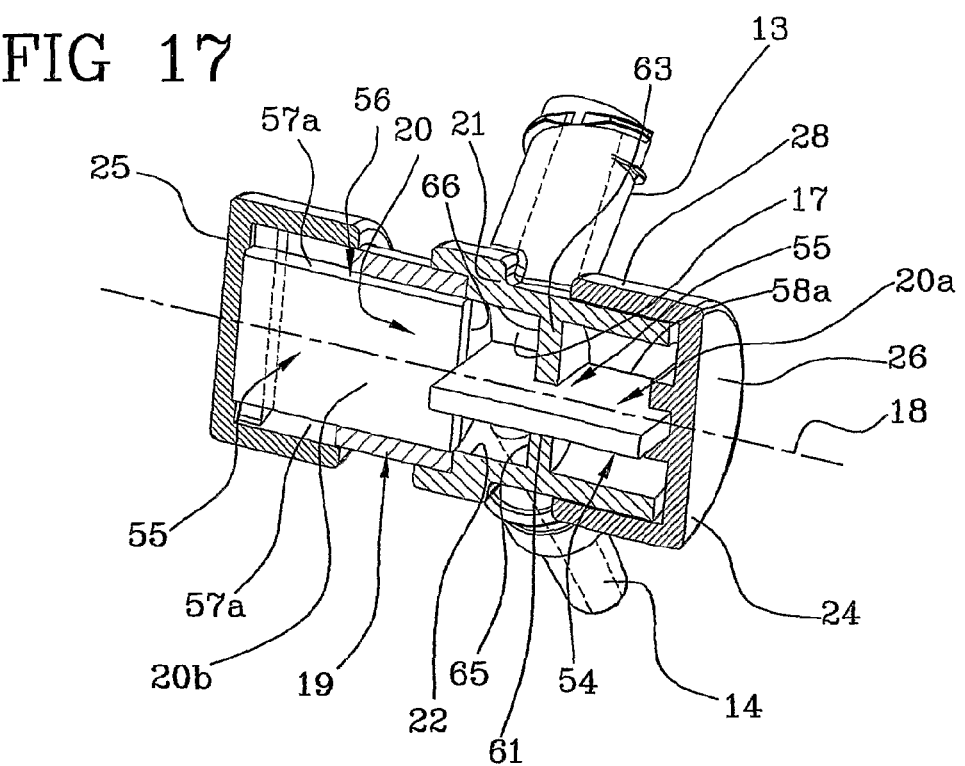
FIG. 17 is a longitudinally sectioned perspective view of the third embodiment shown in FIG. 12.

With reference to the enclosed drawings, reference number 1 denotes an extracorporeal medical device for reversing flow according to the present invention. The device 1 can for instance be used for reversing blood flow in the extracorporeal blood circuit of a blood treatment machine as per the non limiting example of the enclosed FIGS. 9 and 10. In detail the device 1 may be coupled to a blood circuit 2 of a blood processing apparatus 3 (as shown in FIGS. 9 and 10), for instance a machine for one or more of treatments as hemodialysis, hemofiltration, hemodiafiltration, plasmapheresis, oxygenation, ultrafiltration and similar treatments. The apparatus 3 is not described in detail but includes an arterial line 4 for withdrawing blood from a patient, a venous line 5 for returning treated blood to the patient, and a treatment unit 6, such as a filter, hemofilter, plasmafilter or ultrafilter, having a first chamber 7 and a second chamber 9 separated by a semipermeable membrane 6a. The first chamber 7 is connected at one end of said venous and arterial lines. A pump 8, for instance a peristaltic pump, may operate on the arterial line of the blood treatment unit 6. The second chamber 9 of the unit 6 can be connected, at its inlet, to a supply line of fresh dialysis liquid 10 and, at its outlet, to a waste line 11 for discharging used dialysis liquid. The dialysis liquid supply line and the waste line are part of a circuit which is not further detailed as its particulars are not relevant to the present invention. The device for reversing flow 1 is connected with the venous and arterial lines 4 and 5. In detail the lines 4 and 5 have respective patient portions 4a, 5a, interposed between the patient P (only the arm is shown in the mentioned figures) and the device 1, and respective machine portions 4b, 5b interposed between the device and the first (or blood) chamber of treatment unit 6. Portions 4a, 4b, 5a, 5b are also referred to in the claims as: first tubing line 4a, second tubing line 4b, third tubing line 5b, and fourth tubing line 5a.

Figure 2:
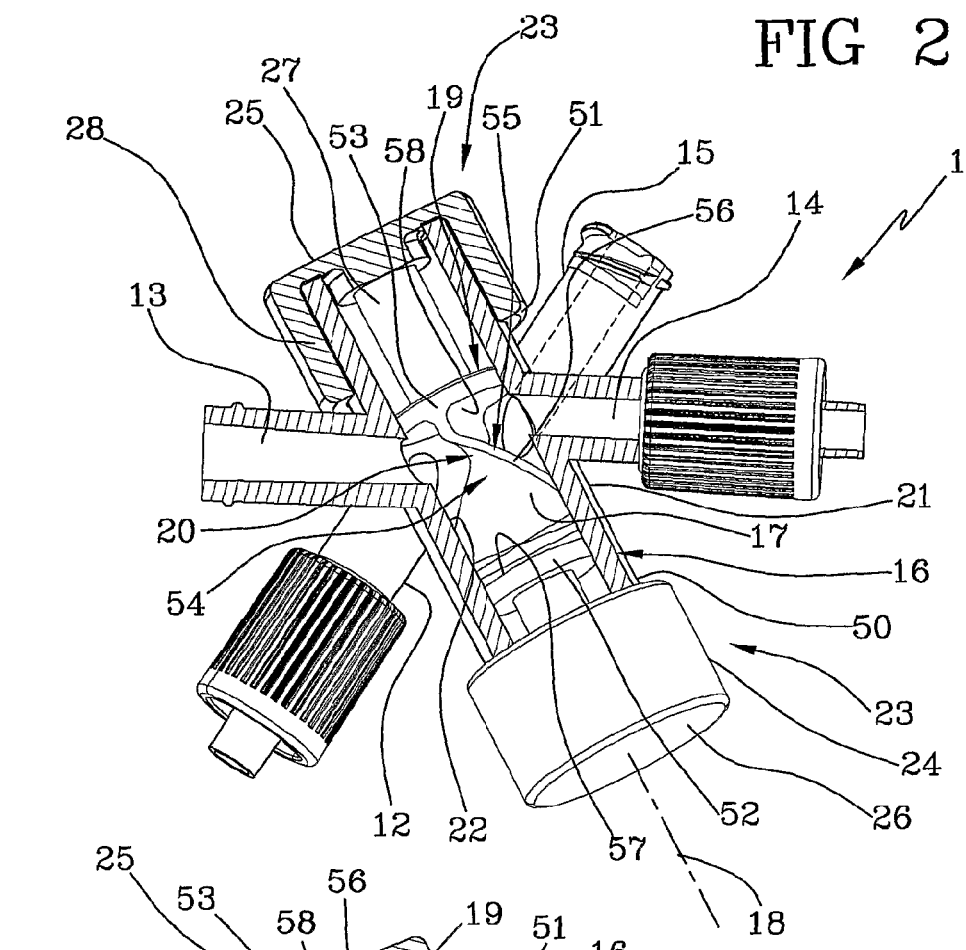
FIG. 2 is a partially sectioned perspective view of a second embodiment of a device for reversing flow in a first operating condition in accordance with the invention.
Figure 3:
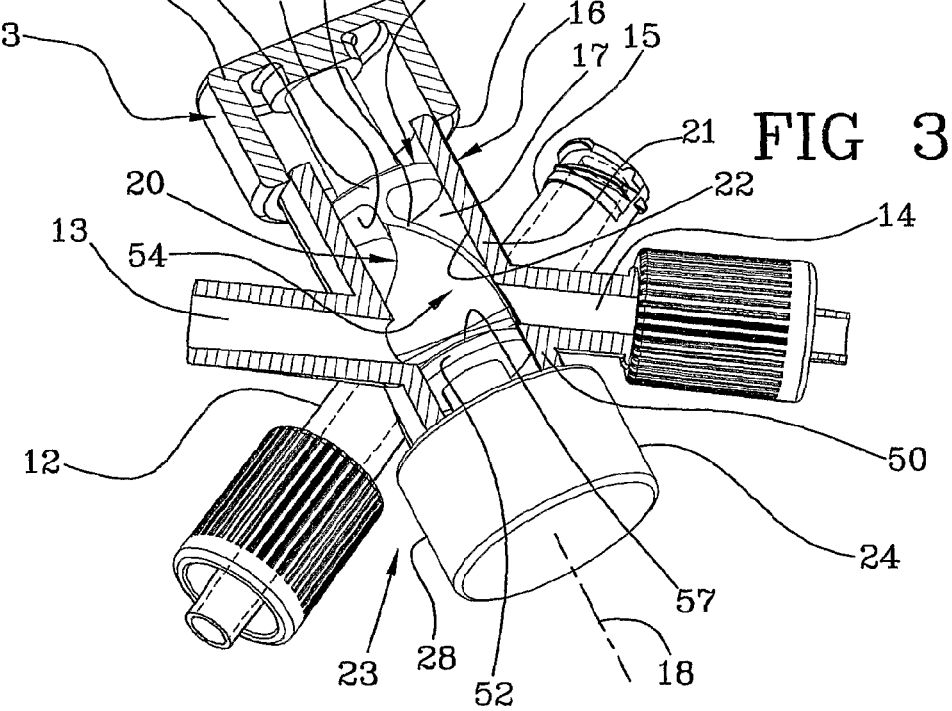
FIG. 3 is a partially sectioned perspective view of a second embodiment of a device for reversing flow in a second operating condition in accordance with the invention.

Notice that while the device 1 shown in FIGS. 9-10 is the second embodiment device of FIGS. 2 and 3 any device according to the present invention can be inserted the same way in the blood circuit 3 of FIGS. 9, 10.

First And Second Embodiments

FIGS. 1A, 1B, 2-5, 9-10

The device 1 presents a housing 16 having at least four ports: a first port 12, connected or connectable by means of a connector piece with portion 4a of line 4, a second port 13, connected or connectable by means of a connector piece with portion 4b of line 4, a third port 14, connected or connectable by means of a connector piece with portion 5a of line 5, and a fourth port 15, connected or connectable by means of a connector piece with portion 5b of line 5. The housing 16 has an internal chamber 17 presenting a longitudinal axis 18, a selector body 19 having at least an active portion 20 movable relative to the housing inside the internal chamber. More in detail the selector body is movable between at least a first position and a second position; in the first position of the selector body, the active portion is positioned relative to the housing so that the first port 12 is in fluid communication with the second port 13 through said chamber while the third port 14 (not shown in FIG. 1 as it is axially opposed to the first port 12) is in fluid communication with the fourth port 15 through said chamber; in said second position of the selector body, the active portion is positioned relative to the housing 16 so that the first port 12 is in fluid communication with the fourth port 15 through the chamber while the second port 13 is in fluid communication with the third port 14 through the chamber 17. The ports can present respective axis oriented transversally to the longitudinal axis of the internal chamber and can be symmetrically arranged on the lateral wall with respect to the longitudinal axis 18. In particular in FIG. 1 the axis of the ports is perpendicular to the longitudinal axis 18 and, moreover, the ports are lying on the same plane and angularly spaced one another by 90°. In the embodiment of FIGS. 2-5, 9 and 10 the axis of the ports is not lying on the same plane: rather the two ports 12 and 14 have an axis generally inclined in towards one end 50 of the device and two ports 13 and 15 have axis inclined towards the opposite end 51 of the same device.

According to a possible aspect of the invention the internal chamber 17 has a lateral wall 21 presenting an inner surface 22 parallel to the longitudinal axis and radially delimiting the internal chamber. The lateral wall inner surface 22 has the shape of a generalized cylinder extending parallel to the longitudinal axis. In the embodiment of FIG. 1, as well as in the remaining embodiments of the enclosed drawing tables, the generalized cylinder has a circular cross section (i.e. the curve defined by the lateral wall inner surface 22 on a section plane perpendicular to the longitudinal axis 18 is a circle). It should however be noticed that the inner surface 22 could also present cross section in the form of a polygon or of an ellipse or of another closed line (in principle regular and symmetric shapes are preferable, however said cross section could also be a closed line of alternative shape). In any case, the cross section of the inner surface 22 should be constant at least for a longitudinal portion of the chamber equal or grater than the axial stroke of the selector body 19 in the chamber 17. Indeed the active portion 20 of the selector body is at least axially displaceable in the chamber 17 parallel to said longitudinal axis as a consequence of the displacement of the selector body 19 between the first and second position.

In further detail the housing 16 comprises a hollow body, for instance a tubular body as in FIG. 1. The housing presents axially opposite open ends 50 and 51, while the selector comprises a first and second terminals 52 and 53 tightly coupled in a sliding manner to the lateral wall inner surface 22. The active portion 20 extends between the first and second terminals and includes a first surface 54, facing the second port 13, a second surface 55, opposite the first surface and facing the fourth port 15, and a peripheral edge 56 connecting the two surfaces 54 and 55 and tightly coupled in a sliding manner to said inner surface 22. Both the first and the second surfaces are continuous and smooth surfaces, thus allowing a gentle fluid flow. On the other hand the peripheral edge comprises two radially opposed edges 56a, 56b (see FIGS. 6 and 7) which allow the necessary liquid tight during operation.

Figure 1A:
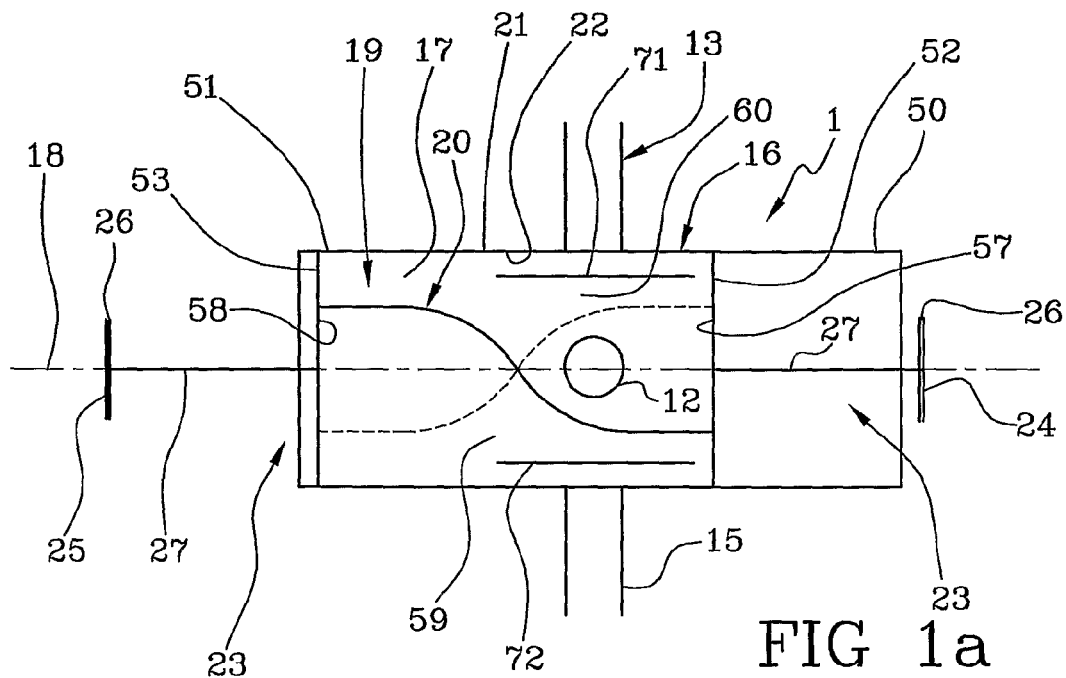
Figure 1B:
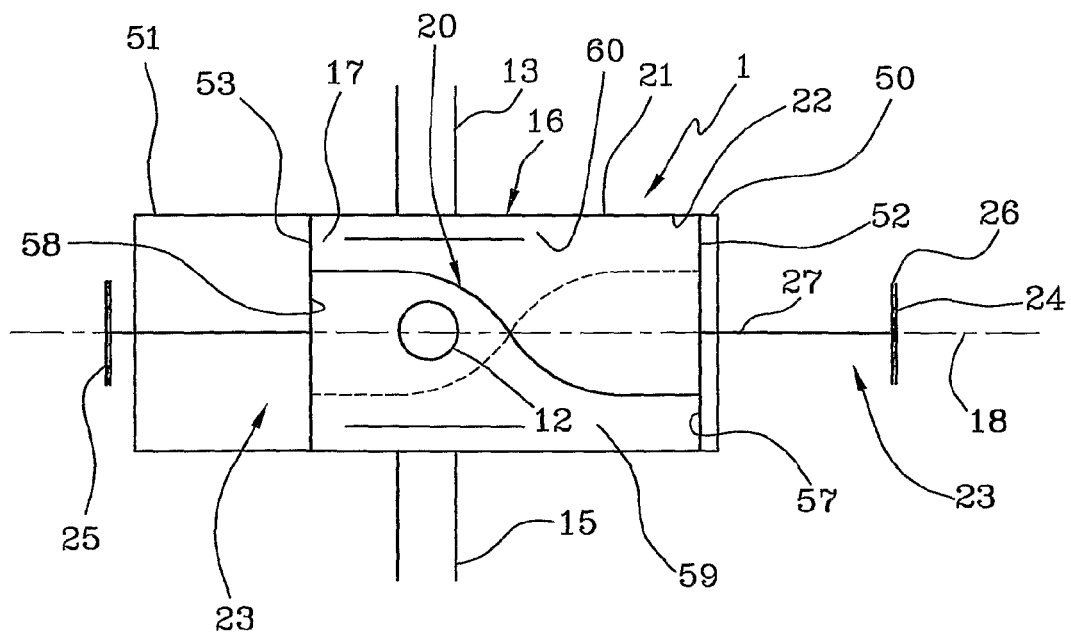
Figure 4:
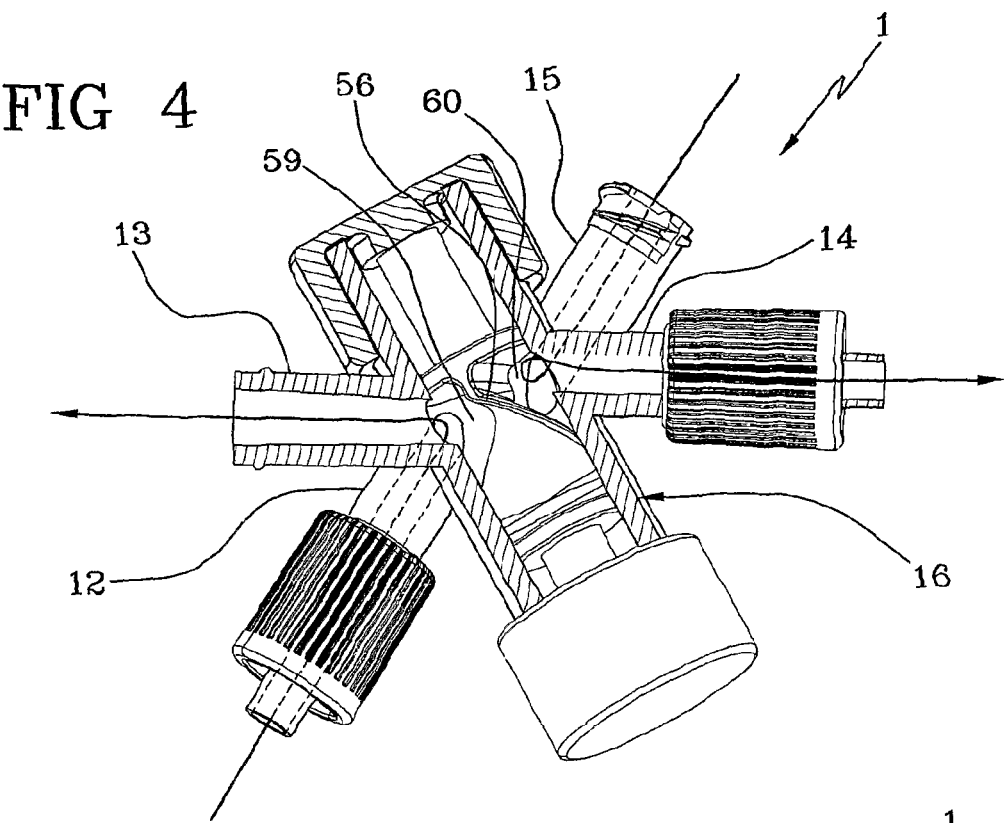
FIG. 4 is a partially sectioned perspective view of a second embodiment of a device for reversing flow in a first operating condition in accordance with the invention, where the arrows represent the circulation paths for the fluid.
Figure 5:
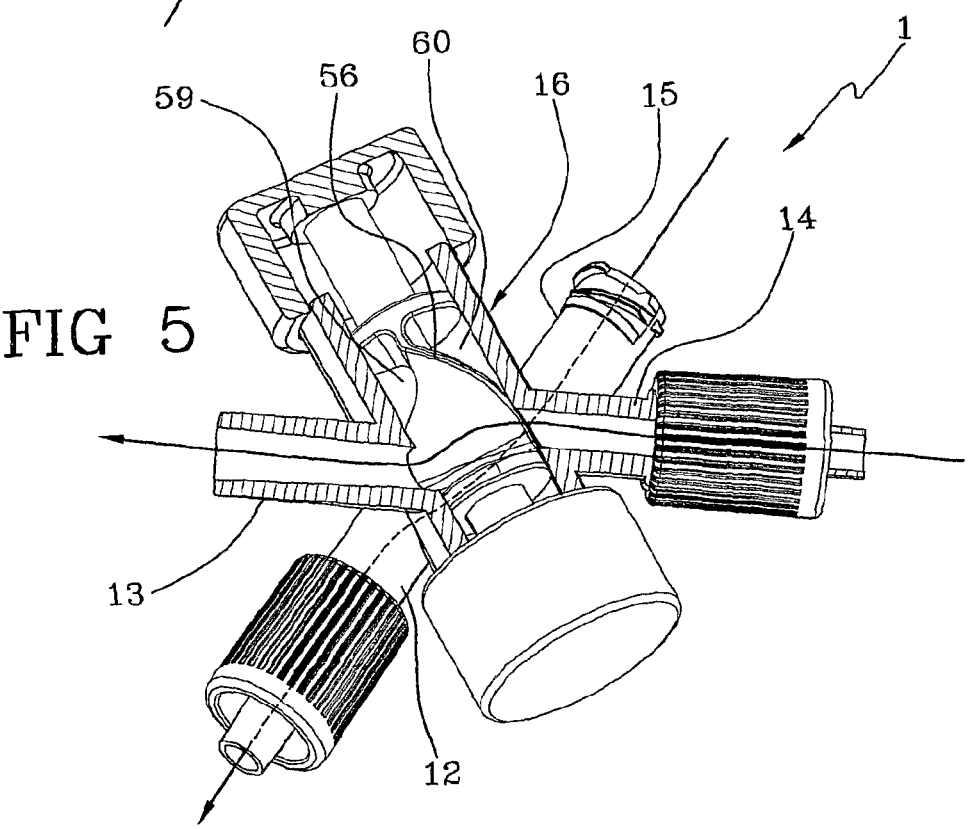
FIG. 5 is a partially sectioned perspective view of a second embodiment of a device for reversing flow in a second operating condition in accordance with the invention where the arrows represent the circulation paths for the fluid.

In the embodiments of FIGS. 1A, 1B, 2-5 and 9, 10 the surfaces 54 and 55 are helicoids and the edges 56a, 56b, have substantially the shape of cylindrical helix extending around the longitudinal axis so as to define on the inner surface correspondingly shaped seal lines. This specific shape allows selection of the ports by axial movement of the selector, while contemporaneously avoiding to stress the blood during the axial movement due to the shape of the surfaces in fluid contact. The first and second terminals 52 and 53 also present respective inner surfaces 57 and 58, facing one another and cooperating with the active portion of the selector and with a portion of the inner surface of the housing to constantly define two tightly separated fluid chambers 59 and 60 extending inside the internal chamber 17 and basically connected with said ports in a different manner depending upon the selected position which determines the axial position of each of said fluid chambers 59 and 60 with respect to the housing and the ports (FIGS. 4 and 5). In the embodiment of FIGS. 1A and 1B, deflectors 71 and 72 are housed in the internal chamber and face the second and the fourth port 13 and 15. The deflectors have at least a portion transversally oriented with respect to an axis of said first port, for instance parallel to the longitudinal axis of the internal chamber, to avoid stagnation of fluid in the areas apart from the ports. In one embodiment the axially opposed ends of the deflectors can also define stopcocks for the selector body.

In order to move the active portion relative to the housing, the flow reversing device comprises means 23 for linearly displacing the selector body between the first and second position. The means 23 for linearly displacing the selector body can be one or two, manually actionable, pushers 24, 25 each connected to a respective terminal 52, 53 of the selector body 19. The pushers can comprise a base 26 extending transversally to the internal chamber longitudinal axis, a rod 27 rigidly connecting the base to the first terminal. In the embodiments of FIGS. 2 to 5, 9 and 10 the pusher also has a collar 28 emerging from said base and coupled in a sliding manner to an external surface of the housing. Due to above structure a user can handle and operate the device 1 with one hand only: basically the thumb can press the pusher and thereby move axially the selector body while the rest of the hand holds the device. When two axially opposite pushers are present the user can press one or the other of the two pushers to move the selector body into the first or second position.

As an alternative embodiment, the means for linearly displacing the selector body can also be automatically controlled. In this case the means 23 would comprise an actuator, such as for instance an hydraulic actuator, a pneumatic actuator, an electric actuator, an electromagnetic actuator, or an actuator of other nature active on said selector body and controlled by a control unit connected to the actuator and controlling the actuator to move the selector body between said first and second positions.

Under a cinematic point of view, while the means for linearly displacing the selector body as per the attached drawings are only working linearly according to a straight axis of actuation, it is not excluded that means, like screw type transmissions or other cinematic solutions involving combined linear and rotational movement, could be envisaged as long as said means are also able to provide the selector body with a straight displacement in the chamber. As example of means 23 controlled automatically, a bi-stable electromechanical linear displacement and magnetic locking device could be used: an electrical winding associated around or in proximity to the housing, with a ferromagnetic selector body or portion of it; the selector body thus has two positions or stable states: retention or locking at one end of the housing can be performed by a permanent magnet and at the other, for instance by a helicoidal spring (of course instead of the helicoidal spring another permanent magnet could be used).

Figure 8:
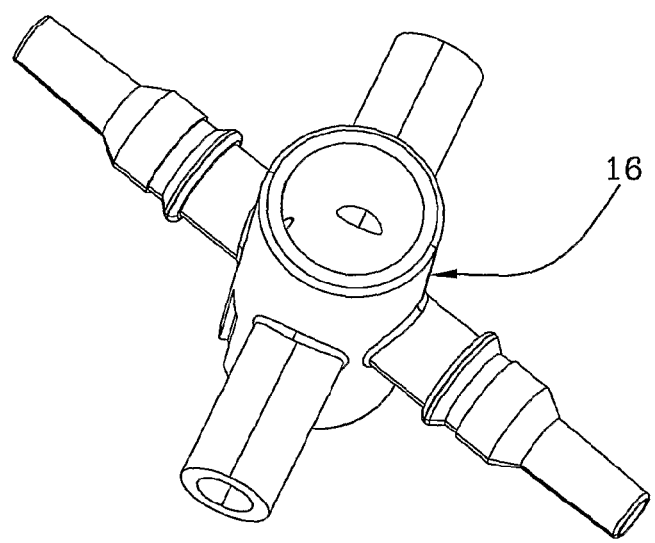
FIG. 8 is a perspective view of an alternative form of a housing which could be used in the device of the present invention.

Housing—Variant of FIG. 8

This figure shows a variant for the housing which could be adopted as housing in any of the embodiments described herein. This housing is substantially similar to that of the embodiment of FIG. 2, but for the ports which present respective axis lying on a common plane which is perpendicular to the longitudinal axis of the internal chamber. Moreover the four ports are divided in two couples of two identical and coaxial ports. This housing could be easily fixed to the front panel of a dialysis machine and automatically controlled.

Figure 6:
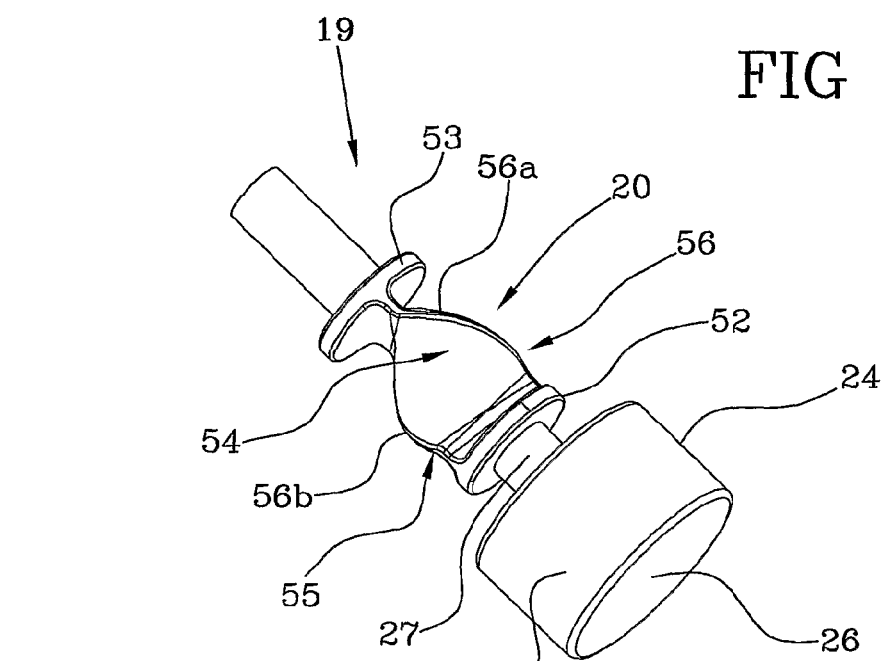
FIGS. 6 and 7 are perspective views of alternative forms of a selector body which could be used in the device of the present invention.
Figure 7:
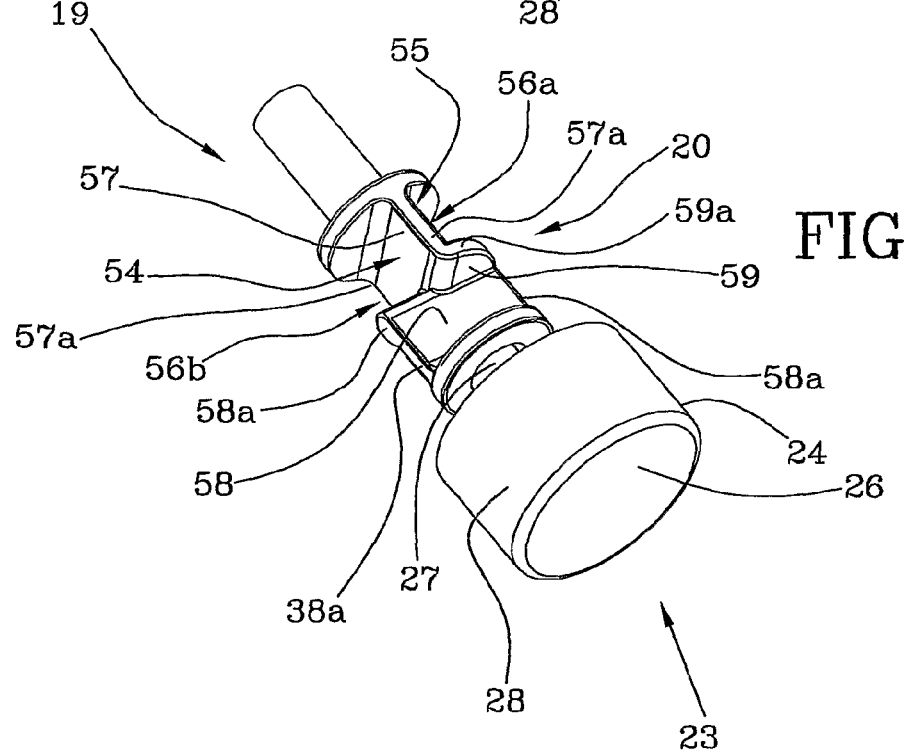

Selector Body—Variants of FIGS. 6 and 7

FIGS. 6 and 7 show alternative non limiting embodiments of a selector body which could be used in the device of the present invention; of course equivalent shapes could be used. In particular the selector body of FIG. 6 or 7 can be used in the second embodiment device shown in FIGS. 2 and 3. The variant of FIG. 6 is basically the one adopted in FIGS. 2 and 3 and reference is made to the above corresponding description; the variant of FIG. 7 shows a selector body 19 having a first surface 54, in use facing the second port 13, a second surface 55, opposite the first surface and in use facing the fourth port 15, and a peripheral edge 56 connecting the two surfaces 54 and 55 and in use working inside the housing tightly coupled in a sliding manner to said inner surface 22. Also in FIG. 7, the peripheral edge comprises two radially opposed edges 56a and 56b which allow the necessary liquid tight during operation. The radially opposed edges 56a, 56b presents a non straight shape when moving axially from one to the other end of the housing or of the active portion. Indeed, as it is visible in FIG. 7 each of the first and second surface 54, 55 present a first flat part and a second flat part 57, 58, the first flat part being transversal, for instance perpendicular, to the second flat part and joined to this latter by a transition part 59 (which in FIG. 7 is in the shape of a quarter of a disc) so that the opposing edges 56a, 56b present each two parallel and non aligned portions 57a, 58a, which are interacting with the inner surface of the lateral wall in correspondence of circumferentially and axially spaced positions. The two parallel portions of each opposing edge are joined by a radial edge 59a of the transition portion. This latter is basically transversal, for instance perpendicular to both flat parts 57, 58. The parts of the means 23 as described for the selector body of FIGS. 2, 3 and 6.

Embodiment of FIGS. 11-17

The device 1 of the third embodiment presents a housing 16 having four ports: a first port 12, connected or connectable by means of a connector piece with portion 4a of line 4, a second port 13, connected or connectable by means of a connector piece with portion 4b of line 4, a third port 14, connected or connectable by means of a connector piece with portion 5a of line 5, and a fourth port 15, connected or connectable by means of a connector piece with portion 5b of line 5. The housing 16 has an internal chamber 17 presenting a longitudinal axis 18, a selector body 19 having at least an active portion 20a, 20b movable relative to the housing inside the internal chamber. More in detail the selector body is movable between at least a first position and a second position; in the first position (FIGS. 12, 14 and 17) of the selector body, the active portion is positioned relative to the housing so that the first port 12 is in fluid communication with the second port 13 through said chamber while the third port 14 is in fluid communication with the fourth port 15 through said chamber; in said second position (FIGS. 13, 15 and 16) of the selector body the active portion is positioned relative to the housing 16 so that the first port 12 is in fluid communication with the fourth port 15 through the chamber while the second port 13 is in fluid communication with the third port 14 through the chamber 17. The ports present respective axis oriented transversally to the longitudinal axis of the internal chamber and can be symmetrically arranged on the lateral wall with respect to the longitudinal axis 18. In particular the axis of the ports in this embodiment is perpendicular to the longitudinal axis 18 and, moreover, the ports are lying on the same plane and angularly spaced one another by 90°.

The internal chamber 17 has a lateral wall 21 presenting an inner surface 22 parallel to the longitudinal axis and radially delimiting the internal chamber. The lateral wall inner surface 22 has the shape of a generalized cylinder extending parallel to the longitudinal axis. In the third embodiment the generalized cylinder has a circular cross section (i.e. the curve defined by the lateral wall inner surface 22 on a section plane perpendicular to the longitudinal axis 18 is a circle). It should however be noticed that the inner surface 22 could also present cross section in the form of a polygon or of an ellipse or of another closed line (in principle regular and symmetric shapes are preferable, however said cross section could also be a closed line of alternative shape). In any case, the cross section of the inner surface 22 should be such to allow the axial stroke of the selector body 19 in the chamber 17. Indeed the active portion 20a, 20b of the selector body is at least axially displaceable in the chamber 17 parallel to said longitudinal axis as a consequence of the displacement of the selector body 19 between the first and second position. The active portion of the third embodiment includes two axially consecutive flat bodies axially guided inside the internal chamber and kept in angularly spaced position (basically in the embodiment shown the two flat body extend on respective planes orthogonal one another). The two flat bodies part of the selector body 19 define a first flat surface 54, a second flat surface 55 opposite the first surface and a peripheral edge 56 having two radially opposed edges, which allow the necessary liquid tight during operation. Each of the opposing edges present two parallel and non aligned portions 57a, 58a, which are interacting with the inner surface of the lateral wall in correspondence of circumferentially and axially spaced positions.

In further detail the housing 16 comprises a hollow body, a first and a second guides 61, 62 for slidingly receiving a respective of said flat bodies. The housing presents a first and a second end wall 63, 64 each extending on a respective side of the internal chamber transversally to the longitudinal axis, said guides being formed by passages in said end walls. The passages realize a fluid tight coupling with the flat bodies so that the chamber 17 is only communicating fluid to the outside via the ports 12, 13, 14, 15.

The first and second end walls present respective inner surfaces 65, 66, facing one another and cooperating with the active portion of the selector and with a portion of the inner surface of the housing to define the two tightly separated fluid chambers.

In this case the selector body separates the inner chamber 17 in the two fluid chambers by means of the flat bodies which selectively enter into the inner chamber 17 according to two transversal planes. In this manner the inner chamber is not axially displacing relative to the ports as in the previously described embodiments, but simply each of the flat bodies cuts the inner chamber in two parts according to two different planes depending upon the axial position of the selector body. In practice in the first position of the selector body only the flat body 20b enters in the chamber 17 to separate it into two parts (tightly separated fluid chambers), while in the second position of the selector body, it is the first flat body 20a entering the chamber 17 to split it into two parts (tightly separated fluid chambers).

As to the means 23, they could be similar to those described in connection with the first and second embodiment. Alternatively as shown in FIGS. 11-17 they could comprise one or two pushers 24, 25 directly acting on one respective of the flat bodies of the selector body 20. As shown in the FIGS. 11-17, each pusher 24, 25 may include a base 26 and a collar 28 slidable along the housing 27.

Of course also in the embodiments of FIGS. 11-17 the inclination of the ports could be different. For instance the ports could be at an angle (different from 90 degrees) to each other as per the embodiment shown in FIG. 2.

REFERENCE NUMBERS extracorporeal medical device 1
blood circuit 2
blood processing apparatus 3
arterial line 4
patient portion of arterial line or first line 4a
machine portion of arterial line or second line 4b
venous line 5
patient portion of venous line or fourth line 5a
machine portions of venous line or third line 5b
treatment unit 6
first chamber 7
pump 8
second chamber 9
membrane 6a
fresh dialysis liquid line 10
waste line 11
first port 12
second port 13
third port 14
fourth port 15
housing 16
internal chamber 17
longitudinal axis 18
selector body 19
active portion 20
flat bodies 20a, 20b
lateral wall 21
inner surface 22 of lateral wall 21
means 23 for linearly displacing the selector body
pushers 24, 25
base 26
rod 27
collar 28
open ends 50 and 51
first and second terminals 52 and 53
first surface 54
second surface 55
radially opposing edges 56a and 56b
spaced portions 57a, 58a of opposing edges 56a, 56b
inner surfaces 57 and 58 of terminals 52 and 53
fluid chambers 59 and 60
first and a second guides 61,62
first and a second end wall 63,64
inner surfaces 65, 66 of the end walls

The invention claimed is:
1. Extracorporeal medical device for reversing flow comprising:

a housing (16) presenting at least four ports (12, 13, 14 and 15) and a lateral wall (21) having an inner surface (22) radially delimiting an internal chamber (17), a selector body (19) having at least an active portion (20) movable relative to the housing inside the internal chamber, between at least a first position and at least a second position, in said first position the active portion being positioned relative to the housing so that the first port (12) is in fluid communication with the second port (13) through said internal chamber (17) while the third port (14) is in fluid communication with the fourth port (15) through said internal chamber (17), and in said second position the active portion being positioned relative to the housing so that the first port (12) is in fluid communication with the fourth port (15) through said internal chamber (17) while the second port (13) is in fluid communication with the third port (14) through said chamber, wherein, as a consequence of the displacement of the selector body between the first and second position, the active portion of the selector body displaces linearly along said inner surface of the lateral wall.

2. Device according to claim 1, wherein the ports (12, 13, 14, 15) present respective axis lying on a common plane, said common plane being perpendicular to the longitudinal axis of the internal chamber.

3. Device according to claim 1, wherein said active portion includes two axially consecutive flat bodies (20a, 20b), which are axially guided inside the internal chamber and kept in angularly spaced positions.

4. Device according to claim 3, wherein said housing includes first and second guides (61, 62) slidingly receiving respective ones of said flat bodies.

5. Device according to claim 4, wherein the housing presents a first and a second end wall (63, 64) each extending on a respective side of the internal chamber transversally to the longitudinal axis, said guides (61, 62) being formed by through passages in said end walls, said passages realizing a fluid tight coupling with the flat bodies and defining for each respective of said flat bodies a corresponding sliding plane, which is at an angle to the sliding plane of the other flat body.

6. Device according to claim 5, wherein said first and second end walls (63, 64) present respective inner surfaces, facing one another and cooperating, in each of said first and second positions, with the active portion of a corresponding one flat body of the selector and with a portion of the inner surface of the housing to define at least two tightly separated fluid chambers.

7. Device according to claim 4, wherein the flat bodies comprise axially opposing edges (56a, 56b) presenting at least two parallel, and transversally spaced portions (57a, 58a), which are interacting with the inner surface of the lateral wall in correspondence of circumferentially and axially spaced positions.

8. Device according to claim 3, comprising one or two pushers (24, 25) directly acting on a respective one of the flat bodies (20a, 20b).

9. Device according to claim 8, wherein each pusher (24, 25) comprises a base (26) and a collar (28) slidable along the housing (16).

10. Extracorporeal medical device for reversing flow comprising:

a housing (16) presenting at least four ports (12, 13, 14 and 15) and a lateral wall (21) having an inner surface (22) radially delimiting an internal chamber (17), a selector body (19) having at least an active portion (20) movable relative to the housing inside the internal chamber, between at least a first position and at least a second position, in said first position the active portion being positioned relative to the housing so that the first port (12) is in fluid communication with the second port (13) through said internal chamber (17) while the third port (14) is in fluid communication with the fourth port (15) through said internal chamber (17), and in said second position the active portion being positioned relative to the housing so that the first port (12) is in fluid communication with the fourth port (15) through said internal chamber (17) while the second port (13) is in fluid communication with the third port (14) through said chamber, wherein, as a consequence of the displacement of the selector body between the first and second position, the active portion of the selector body displaces at least axially along said inner surface of the lateral wall;

wherein said active portion includes two axially consecutive flat bodies (20a, 20b), which are axially guided inside the internal chamber and kept in angularly spaced positions.

* * * * *